United States Patent
Huszár et al.

(10) Patent No.: US 9,382,223 B2
(45) Date of Patent: Jul. 5, 2016

(54) PROCESS FOR PREPARATION OF DRONEDARONE BY OXIDATION OF A HYDROXYL GROUP

(71) Applicant: SANOFI, Paris (FR)

(72) Inventors: Csaba Huszár, Budapest (HU);
Adrienn Hegedus, Budapest (HU);
Zsolt Dombrády, Budapest (HU)

(73) Assignee: SANOFI, Paris (FR)

(*) Notice: Subject to any disclaimer, the term of this patent is extended or adjusted under 35 U.S.C. 154(b) by 0 days.

(21) Appl. No.: 14/377,484

(22) PCT Filed: Feb. 14, 2013

(86) PCT No.: PCT/IB2013/001220
§ 371 (c)(1),
(2) Date: Aug. 7, 2014

(87) PCT Pub. No.: WO2013/124745
PCT Pub. Date: Aug. 29, 2013

(65) Prior Publication Data
US 2016/0009678 A1    Jan. 14, 2016

(30) Foreign Application Priority Data
Feb. 22, 2012 (EP) .................................. 12462006

(51) Int. Cl.
*C07D 307/81* (2006.01)
(52) U.S. Cl.
CPC .................................. *C07D 307/81* (2013.01)
(58) Field of Classification Search
CPC .................................................. C07D 307/81
See application file for complete search history.

(56) References Cited

U.S. PATENT DOCUMENTS

| | | | |
|---|---|---|---|
| 3,577,441 A | 5/1971 | Kaminsky et al. | |
| 3,657,350 A | 4/1972 | Mooradian et al. | |
| 3,937,737 A | 2/1976 | Eiglmeier | |
| 4,243,405 A | 1/1981 | Balasubramanyan et al. | |
| 4,666,931 A | 5/1987 | Ohishi et al. | |
| 5,066,803 A | 11/1991 | D'Ambra et al. | |
| 5,223,510 A * | 6/1993 | Gubin et al. | 514/299 |
| 6,555,697 B1 | 4/2003 | Schlama | |
| 6,828,448 B2 | 12/2004 | Fino et al. | |
| 6,846,936 B2 | 1/2005 | Biard | |
| 6,855,842 B1 | 2/2005 | Schlama et al. | |
| 6,949,583 B2 | 9/2005 | Assens et al. | |
| 6,984,741 B2 | 1/2006 | Magerlein | |
| 7,148,240 B2 | 12/2006 | Assens et al. | |
| 7,312,345 B2 | 12/2007 | Gutman et al. | |
| 7,517,876 B2 | 4/2009 | Klein et al. | |
| 8,143,269 B2 | 3/2012 | Whitten et al. | |
| 8,501,971 B2 | 8/2013 | Friesz et al. | |
| 8,658,808 B2 | 2/2014 | Kretzschmar et al. | |
| 8,658,809 B2 | 2/2014 | Friesz et al. | |
| 8,674,121 B2 | 3/2014 | Kretzschmar et al. | |
| 8,686,180 B2 | 4/2014 | Bon et al. | |
| 8,748,636 B2 | 6/2014 | Bailly et al. | |
| 8,796,489 B2 | 8/2014 | Bailly et al. | |
| 8,816,103 B2 | 8/2014 | Friesz et al. | |
| 8,871,956 B2 | 10/2014 | Bailly et al. | |
| 8,884,033 B2 | 11/2014 | Bon et al. | |
| 8,889,734 B2 | 11/2014 | Friesz et al. | |
| 8,927,743 B2 | 1/2015 | Vishnu Newadkar et al. | |
| 8,962,869 B2 | 2/2015 | Grimaud et al. | |
| 9,024,046 B2 | 5/2015 | Friesz et al. | |
| 9,174,958 B2 | 11/2015 | Friesz | |

(Continued)

FOREIGN PATENT DOCUMENTS

| CN | 101838252 A | 9/2010 |
|---|---|---|
| CN | 101993427 A | 3/2011 |

(Continued)

OTHER PUBLICATIONS

Ladge et al., 2014, caplus an 2014:538118.*
Stahl, P.H. et al. (2005). "List of Pharmaceutically Acceptable Acids," The Royal Society of Chemistry in *Handbook of Pharmaceutical Salts: Properties, Selection and Use*, Electronic Supplementary Material for CrystEngComm, one page.
U.S. Appl. No. 14/863,206, filed Sep. 23, 2015, by Friesz et al.
U.S. Appl. No. 14/945,222, filed Nov. 18, 2015, by Friesz et al.
U.S. Appl. No. 14/946,510, filed Nov. 19, 2015, by Friesz et al.
Abramenko et al. (1975). "Polymethine Dyes—Furo[2,3-g] Benzothiazole Derivatives," *Chemistry of Heterocyclic Compounds* 11:1361-1364.
Adams et al. (1951). Quinone imides. IV. P-Quinone monosulfonimides. *Journal of the American Chemical Society* 73:1145-1149.

(Continued)

*Primary Examiner* — Sun Jae Yoo
(74) *Attorney, Agent, or Firm* — Morrison & Foerster LLP

(57) ABSTRACT

The invention relates to a novel process for the preparation of dronedarone (I) and pharmaceutically acceptable salts thereof (formula I), which comprises oxidizing a compound of formula (VI), or a salt thereof and the obtained product is isolated and, if desired, converted into a pharmaceutically acceptable salt thereof. Further aspects of the invention include the novel intermediary compound of formula (VI) and process for the preparation thereof.

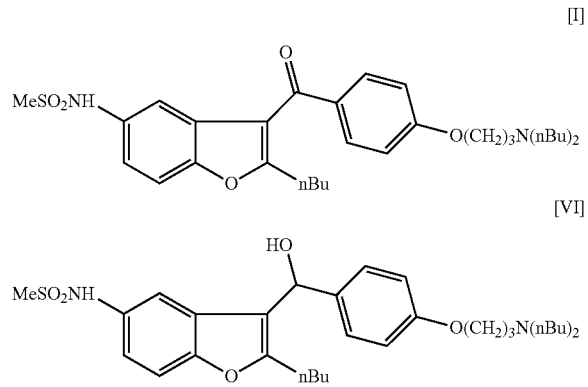

4 Claims, No Drawings

(56) References Cited

U.S. PATENT DOCUMENTS

| | | | |
|---|---|---|---|
| 9,174,959 | B2 | 11/2015 | Friesz et al. |
| 9,238,636 | B2 | 1/2016 | Huszar et al. |
| 2008/0033209 | A1 | 2/2008 | Szarvas et al. |
| 2010/0273764 | A1 | 10/2010 | Andrews et al. |
| 2013/0023678 | A1 | 1/2013 | Priem et al. |
| 2013/0109868 | A1 | 5/2013 | Friesz |
| 2014/0018553 | A1 | 1/2014 | Grimaud et al. |
| 2014/0081035 | A1 | 3/2014 | Friesz et al. |
| 2014/0114081 | A1 | 4/2014 | Friesz et al. |
| 2015/0005515 | A1 | 1/2015 | Friesz et al. |
| 2015/0018568 | A1 | 1/2015 | Friesz |
| 2015/0031901 | A1 | 1/2015 | Bon et al. |
| 2015/0031902 | A1 | 1/2015 | Huszar et al. |

FOREIGN PATENT DOCUMENTS

| | | |
|---|---|---|
| EP | 0 471 609 A1 | 2/1992 |
| EP | 0 735 083 A1 | 10/1996 |
| FR | 2 833 259 A1 | 6/2003 |
| WO | WO-96/05190 A1 | 2/1996 |
| WO | WO-02/48078 A1 | 6/2002 |
| WO | WO-02/48132 A1 | 6/2002 |
| WO | WO-03/040120 A1 | 5/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/133637 A2 | 11/2007 |
| WO | WO-2007-133637 A3 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136501 A1 | 12/2010 |
| WO | WO-2010/136502 A1 | 12/2010 |
| WO | WO-2011/070380 A1 | 6/2011 |
| WO | WO-2011/099010 A1 | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/044658 A3 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-03/048144 A2 | 6/2013 |
| WO | WO-03/048144 A3 | 6/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Adams et al. (1956). "Quinone Imides. XXXIX. Adducts of Quinone Monoimides and Conversion of Active Methylene Adducts to Benzofurans," *J. Am. Chem. Soc.* 78(3):658-663.
Alcaraz et al. (2004). "Novel N-Aryl and N-Heteroaryl Sulfamide Synthesis via Palladium Cross Coupling," *Organic Letters* 6(16):2705-2708.
Ando et al. (1982). "Motion at the Active Site of Tosylchymotrypsin," *Journal of the American Chemical Society* 104(11):3172-3178.
Anjanappa et al. (2008). "2-(Trimethylsilyl)ethanesulfonyl Amide as a New Ammonia Equivalent for Palladium—Catalyzed Amination of Aryl Halides," *Tetrahedron Letters* 49:4585-4587.
Bartoli et al. (1991). "Unexpected Elimination to α,β-Alkynylketones in the Reaction of Dianions of 1-Arylenaminones with Trimethylchlorosilane," *Tetrahedron Letters* 32(48):7091-7092.
Batra et al. (2001). "Syntheses and Biological Evaluation of Alkanediamines as Antioxidant and Hypolipidemic Agents," *Bioorganic & Medicinal Chemistry* 9(12):3093-3099.
Bavin (1973). "2-Aminofluorene," *Org. Syn. Coll.* 5:30.
Berthold et al. (2002). "Transfer Hydrogenation in Ionic Liquids under Microwave Irradiation," *Syn.* 1607-1610.
Boovanahalli et al. (2004). "Application of Ionic Liquid Halide Nucleophilicity for the Cleavage of Ethers: A Green Protocol for the Regeneration of Phenols from Ethers," *Journal of Organic Chemistry* 69:3340-3344.
Bourgery et al. (1981). "Synthesis and Antiarrhythmic Activity of New Benzofuran Derivatives," *Journal of Medicinal Chemistry* 24(2):159-167.
Burton et al. (2003). "Palladium-Catalyzed Intermolecular Coupling of Aryl Chlorides and Sulfonamides under Microwave Irradiation," *Organic Letters* 5(23):4373-4376.
Castellino et al. (1984). "Synthesis of Benzofurans from Oxygenated Phenoxyamines," *Journal of Organic Chemistry* 49:4399-4404.
Chauhan et al. (2004). "Microwave assisted dealkylation of alkyl aryl ethers in ionic liquids," *Journal of Chemical Research*, pp. 693-694.
Cheng et al. (2007). "Facile Cleavage of Ethers in Ionic Liquid," *Bulletin of the Chemical Society of Japan* 80(10):2008-2010.
Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].
Delahay et al. (2007). "Past and Recent Approaches of Preparing Fe-ZSM-5," *Current Topics in Catalysis* 6:19-33.
Douglass (1959). "Some New Reactions of Methanesulfenyl Chloride," *Journal of Organic Chemistry* 24:2004-2006.
Denmark et al. (2008). "Lewis base catalysis in organic synthesis," *Angew. Chem. Int. Ed.* 47(9):1560-1638.
Fennel (1958). "Quinoline Analogs of Podophyllotoxin. I. Preliminary Experiments. Syntheses of Some 4-Phenylquinoline Derivatives," *J. Org. Chem.* 23:432-434.
Fieser et al. (1967). "Reagents for Organic Synthesis," John Wiley & Sons, pp. 703-705.
Fontana (2008). "Syntheses of (R,S)-Naproxen and its 6-O-Desmethyiated metabolite labelled with 2H," *J. Labelled Compounds and Radiopharma.* 51:239-241.
Gilow et al. (Jun.-Jul. 1991). "Sulfenylation of Some Pyrroles and Indoles," *J. Het. Chem.* 28:1025-1034.
Groves (1972). "The Friedel—Crafts Acylation of Alkenes," *Chem. Soc. Rev.* 1:73-97.
Gutowski et al, (2005). "Prediction of the Formation and Stabilities of Energetic Salts and Ionic Liquids Based on ab lnitio Electronic Structure Calculations," *The Journal of Physical Chemistry B* 109:23196-23208.
Haddadin et al. (1976). "Reaction to Benzofurazan Oxide with Unsymmetrical 1, 3-Diketones: Steric Polar Effects," *Tetrahedron* 32:719-724.
Hauser et al. (1948) "Alkaline cleavage of unsymmetrical β-diketones. Ring opening of acylcyclohexanones to form ε-acylcaproic acids," *Journal of the American Chemical Society*. 70:4023-4026.
Headley et al. (2006). "Dynamic Solvation in Imidazolium-Based Ionic Liquids on Short Time Scales," *Journal of Physical Chemistry* 110:9549-9554.
Horton et al. (1967). "Reactions With Reactive Alkyl Halides," *J. Meth. In Enzymology* 11:556-565.
Ikawa et al. (2007). "Pd-Catalyzed Amidations of Aryl Chlorides Using Monodentate Biaryl Phosphine Ligands: A Kinetic, Computational, and Synthetic Investigation," *Journal of the American Chemical Society* 129:13001-13007.

(56) References Cited

OTHER PUBLICATIONS

Imori et al. (2006). "Efficient Demethylation of N,N-Dimethylanilines with Phenyl Chloroformate in Ionic Liquids," *Synlett.* 16:2629-2632.

International Search Report mailed on Jan. 22, 2014, for PCT Patent Application No. PCT/IB2013/001220, filed on Feb. 14, 2013, four pages.

Johnson Matthey Handbook of Pharmaceutical Catalysis, 2009, pp. 1-106.

Joshi et al. (1986). "Some New Fluorinated β-Ketoamines and Their Copper Complexes," *Synth. React. Inorg. Met.-Org. Chem.* 16(7):1009-1024.

Krongauz et al. (1986). Poly(anilophenylquinoxaline)s. *Inst. Elementoorg. Soedin.* 28(4):771 (Abstract).

Kurti et al. (2005). Strategic Applications of Named Reactions in Organic Synthesis. El Sevior, pp. 448-449.

Kwiatkowski et al. (1978). "Metal Benzoylpivaloylmethanates, Part I. Free Ligands and Copper(II) Chelates," *Transition Met. Chem.* 3:305-308.

Laszlo et al. (1987). "Catalysis of Friedel-Crafts Alkylation by a Montmorillonite Doped with Transition-Metal Cations," *Helvetica Chimica Acta* 70:577-586.

Liu et al. (2004). "Cleavage of Methyl Ethers of Flavones by Chloroaluminate Ionic Liquid," *Synthetic Communications* 34:3209-3218.

Majdik (1985). "Studiul reactiei de ciclizare a orto-hidroxibenzilfenilcetonelor in benzofuran derivati," *Revista de Chimie* 36(8):760-761 (with English Translation).

Majdik et al. (1989). "Prepararea unor 2-(aril)-nitrobenzofurani din 0-(nitrofenil)-acetofenonoxime," *Revista de Chemie*, vol. 40, No. 8, pp. 689-693 (with English Translation).

Majdik et al. (1989). "0-Arilarea cetoximelor cu nitroclorbenzeni," *Revista de Chemie*, vol. 40, No. 6, pp. 490-493 (with English Translation).

March (Jul. 1, 1992). "Aromatic Electrophilic Substitution," Chapter 11 in *Advanced Organic Chemistry, Reactions, Mechanism and Structure*, 4th edition, Wiley Interscience, pp. 538-542.

March (Jul. 1, 1992). "Aliphatic Nucleophilic Substitution," Part 2 in *Advanced Organic Chemistry, Reactions, Mechanism and Structure*, 4th edition, Wiley Interscience, pp. 442.

Marvel et al. (1941). "Diphenylacetic Acid," *Org. Synth. Coll.* vol. 1, 224-225.

Mehrotra et al. (2001). "Search for new chemical entities as menses inducing agents," *Contraception* 64:187-191.

Munch et al. (1946). "The Preparation of Some α-Dialkylamino-ω-Methylaminoalkanes," *J. Am. Chem. Soc.* 68:1297-1299.

Nagy et al. (2007). "Isomorphous Substitution in Zeolites," *Mol. Sieves* 5:365-478.

Nakamura et al. (2004). "Pyrazole Derivatives as new potent and selective 20-hydroxy-5,6,11,14-Eicosatetraenoic Acid Synthase Inhibitors," *Bioorganic Medic. Chem.* 12:6209-6219.

Pal et al. (2007). "Synthesis of monohydroxy-functionalized triphenylene discotics: green chemistry approach," *Tetrahedron* 63:6874-6878.

Roshchin et al. (1998). "Synthesis of Benzofurans via Pd2+-Catalyzed Oxidative Cyclization of 2-Allylphenols," *Journal of Organometallic Chemistry* 560(1-2):163-167.

Sanfilippo (1988). "Synthesis of (aryloxy)alkylamines. 1. Novel antisecretory agents with H+K+-ATPase inhibitory activity," *J. Med. Chem.* 31(9):1778-1785.

Serajuddin (2007). "Salt formation to improve drug solubility," *Advanced Drug Delivery Reviews* 59:603-616.

Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," *Indian Journal of Chemistry* 208:234-237.

Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.

Ślusarska et al. (Feb. 1981). "One-Pot Phase-Transfer-Catalysed N-Alkylation of Diphenylphosphinamide with Alcohols in the Presence of Methanesulfonyl Chloride," *Synthesis* 155-156.

Son et al. (1989). "Stereochemical Mechanism of Iodoacetic Acid Mediated Decomposition of $_L$-Methionine to $_L$-Homoserine Lactone," *Journal of the American Chemical Society* 111(4):1363-1367.

Sun et al. (2004). "N-{2[2-( 4-Phenylbutyl)benzofuran-4-yl]cyclopropylmethyl}-acetamide: an orally bioavailable melatonin receptor agonist," *Bioorganic & Medicinal Chemistry Letters* 14:5157-5160.

Tanaka (1967). "Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives," *Bulletin of the Chemical Society of Japan* 40(7):1724-1726.

Thornber (1979). "Isosterism and Molecular Modification in Drug Design." *Chem. Soc. Rev.* 8:563-580.

Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.

Wamser et al. (1989). "Kinetics and Mechanisms for the Two-phase Reaction between Aqueous Aniline and Benzoyl Chloride in Chloroform, with and without Pyridine Catalysis," *J. Org. Chem.* 54:150-154.

Weissman et al. (2005). "Recent advances in ether dealkylation," *Tetrahedron* 61:7833-7863.

Weitkamp et al. (1986). "Isomorphe Substitution in Zeolithen: Katalyse an Boro-, Alumo-und Galio-Silicaten mit ZSM-5-Strukter," *Chem. Ing. Tech.* 58(12):969-971 (with English Translation).

Wikipedia. (Nov. 5, 2012). "Reduction of Nitro Compounds."

Wu et al. (2004). "Immobilization of HX: [Hmim]X as Halogenating Agent, Recyclable Catalyst and Medium for Conversion of Alcohols to alkyl halides," *Chinese J. Chem.* 22:619-621.

Wuts (2006). Greene's Protective Groups in Organic Synthesis, Fourth Edition, John Wiley and Sons, Chapter 7, Protection for the Amino Group, pp. 696-926.

Yang et al. (2009). "Structure-Based Virtual Screening for Identification of Novel 11 β-HSD1 Inhibitors," *European J. of Medicinal Chem.* 44(3):1167-1171.

Yin et al. (2000). "Palladium-Catalyzed Intermolecular Coupling of Aryl Halides and Amides," *Organic Letters* 2(8):1101-1104.

Yin et al. (2002). "Pd-Catalyzed Intermolecular Amidation of Aryl Halides: The Discovery that Xantphos Can Be Trans-Chelating in a Palladium Complex," *Journal of the American Chemical Society* 124:6043-6048.

Zasshi (1956). "Studies on the Syntheses of Phenothiazine Derivatives. I. Syntheses of N-Substituted Phenothiazines by Tosylates," *J. Pharm. Soc. of Japan* 76:637-640 (with English Translation).

U.S. Appl. No. 14/377,484, filed Aug. 7, 2014, by Huszar et al.

U.S. Appl. No. 14/403,528, filed Nov. 24, 2014, by Huszar et al.

\* cited by examiner

PROCESS FOR PREPARATION OF DRONEDARONE BY OXIDATION OF A HYDROXYL GROUP

CROSS-REFERENCE TO RELATED APPLICATIONS

This application is a National Phase application under 35 U.S.C. §371 of International Application No. PCT/IB2013/001220 filed Feb. 14, 2013 and claims the benefit of EP Application No. 12462006.3 filed Feb. 22, 2012, the disclosures of which are incorporated herein by reference in their entirety.

FIELD OF THE INVENTION

The invention relates to a novel process for the preparation of dronedarone and pharmaceutically acceptable salts thereof, to novel intermediary compounds used in this process and their preparation.

TECHNICAL BACKGROUND

Dronedarone, i.e. N-[2-n-butyl-3-[4-[3-(di-n-butylamino)propoxy]benzoyl]-1-benzofuran-5-yl]-methanesulfonamide, having the formula (I):

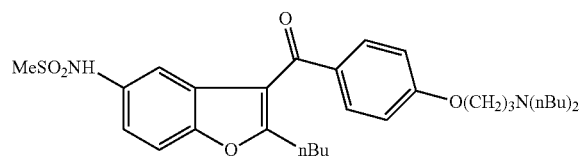

(I)

is a known drug for the treatment of arrhythmia (EP0471609).

There are some known processes for the preparation of dronedarone as follows:

In EP 0471609 the following scheme is disclosed for the preparation of dronedarone
[Process A]

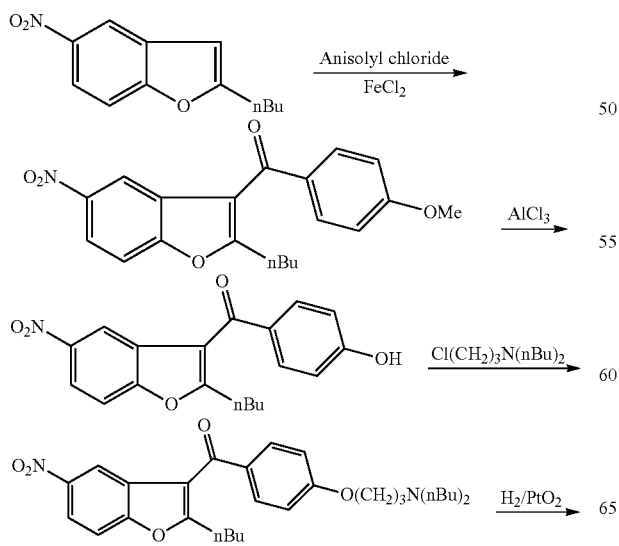

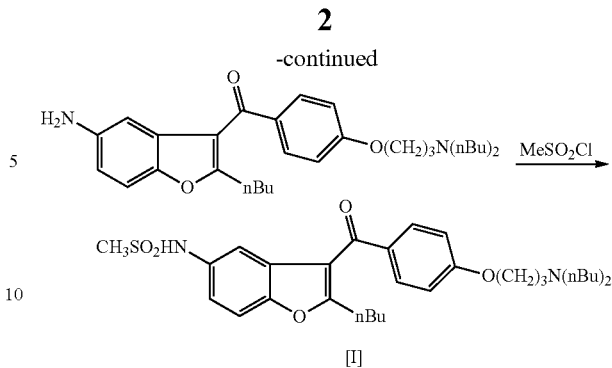

[I]

The above mentioned patent description discloses some new intermediary compounds, too.

In WO 02/48078 the following scheme is disclosed for the preparation of dronedarone
[Process B]:

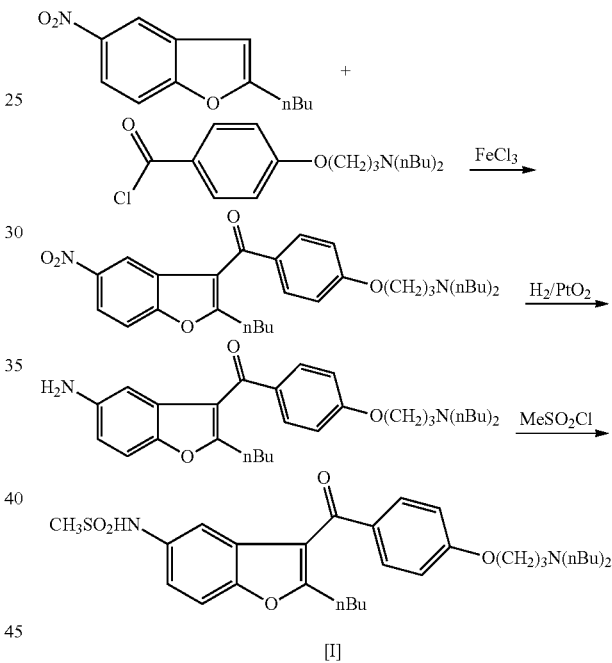

[I]

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so-called superconvergent route. In the first step of it 5-amino-2-butylbenzofuran

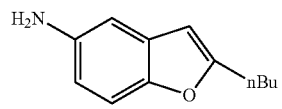

is mesylated and the obtained 2-butyl-5-methanesulfona-mido-benzofuran (in HCl salt form) is further reacted in the next step as follows:

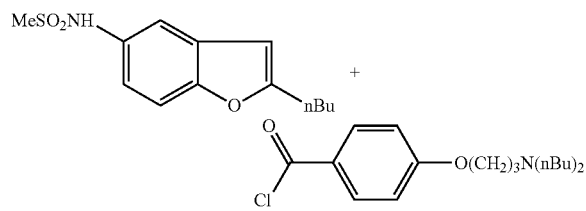

In this process the order of reaction steps are altered, the reduction and the methansulfonylation steps are performed at the beginning part of the procedure. Besides the reaction route for preparation of dronedarone, the starting material 2-butyl-5-methansulfonamido-benzofuran and its preparation are also claimed.

From among the mentioned procedures the first one [Process A] is the so-called linear synthesis. In this way of procedure the different parts of the dronedarone are stepwise built up on the starting compound. This method is the least economical because the continuous step by step building of the chemical groups is performed on more and more complicated and expensive molecules, which raises the costs of the preparation.

Furthermore it comprises complicated and harmful reaction steps because aluminium chloride is used in the cleaving reaction of the methoxy group which makes the industrial feasibility more complicated.

In WO 02/48078 (Process B) a shorter synthetic route is disclosed which makes this process more economical, but its last reaction step remained, the methansulfonylation reaction of the amino group. This reaction step (see the method described in example 6 of WO02/48078) is complicated and gives a low yield of only 61.6%. Pure product can be expected after purification using chromatographic column purification, which is necessary because of the separation difficulties of the bis-methanesulfonylated product.

The process disclosed in WO 02/48132 (process C) is simpler and more economical taking into consideration the number of the reaction steps. Unfortunately, in the last reaction step rather impure dronedarone.HCl (hydrochloride salt) is formed which is the obvious consequence of the presence of the dibutylamino group in the Friedel-Crafts reaction. According to Examples 3 and 4, the crude dronedarone hydrochloride salt is prepared with a yield of 90% which is further purified and finally the crude dronedarone base is produced with a yield of 86%. This base is reacted with hydrogen chloride gas dissolved in isopropanol which results in pure dronedarone hydrochloride salt. No yield is given for this reaction step. According to example 5 crude dronedarone hydrochloride salt is prepared with a yield of 90%, which is washed with water and reacted with hydrogen chloride gas dissolved in isopropanol, resulting dronedarone hydrochloride salt again. The quality of this product is not known. However, since neither the components used in the Friedel-Crafts reaction nor the resulting products and by-products are soluble in water, the washing step with water cannot result any purification apart from the removal of inorganic salts.

There is another drawback of this process, namely, a dimesylated side-product is formed in the mesylation reaction of the 5-amino-2-butyl-benzofuran. The purification is carried out by crystallization which has a yield of 78.5%.

It is an object of the present invention to provide a novel process for the preparation of dronedarone (I), starting from known and commercially available materials, applying simple, environmentally compatible reagents and solvents, to afford high overall yields and good purity of the product.

SUMMARY OF THE INVENTION

The main aspect of the invention is a process for preparation of dronedarone (I) and pharmaceutically acceptable salts thereof

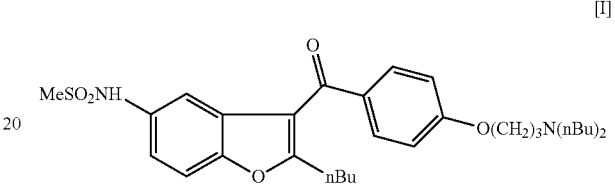

which comprises oxidizing a compound of formula (VI), or a salt thereof

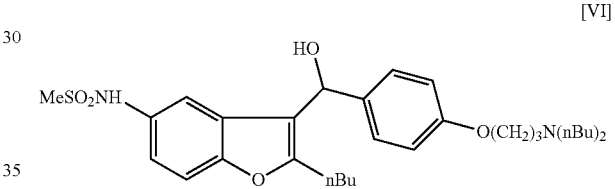

and the obtained product is isolated and, if desired, converted into a pharmaceutically acceptable salt thereof.

We have surprisingly found that the formation of the oxo group in the last step by oxidation of an OH group which is formed by aldol condensation of substituted benzofuran and an aldehyde, has several benefits. Namely, the advantages of this process compared to the previously mentioned [A] and [B] processes are that the Friedel-Crafts acylation of 2-butyl-5-nitrobenzofuran can be avoided and the process does not use harmful reagents such as $AlCl_3$ or $FeCl_3$. Furthermore, the final oxidation step with hydrogen peroxide is a pure process with good isolated yield.

Further aspects of the invention include the compound of formula (VI) as a new compound, its salts and process for the preparation thereof (see below in the "Detailed description of the invention" part).

DETAILED DESCRIPTION OF THE INVENTION

Therefore the present invention relates to a process for the preparation of dronedarone and pharmaceutically acceptable salts thereof. The whole process—starting from known compounds—reads as follows:

(a) a compound of formula (II) (N-(2-butyl-1-benzofuran-5-yl)methanesulfonamide) is reacted with the compound of formula (V) in the presence of strong acid or base catalyst to obtain a compound of formula (VI):

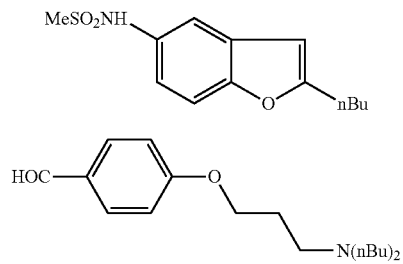

(b) the compound of formula (VI) (N-(2-butyl-3-{[4-(3-dibutylamino-propoxy)-phenyl]-hydroxymethyl}-benzofuran-5-yl)-methanesulfonamide) is oxidized to obtain dronedarone (I), and the obtained product is isolated and, if desired, converted into a pharmaceutically acceptable salt thereof.

The intermediate (VI) is a new compound and is isolated in pure solid form. Said compound, its salts and its preparation process [i.e. the above step (a)] form further objects of the invention.

Compound of formula (V) is known from J. Med. Chem. 1988, 31 (9) 1778. It can be prepared as described in the following:

a compound of formula (III) (4-hydroxybenzaldehyde) is reacted with a compound of formula (IV) (dibutylamino propylchloride HCl salt)

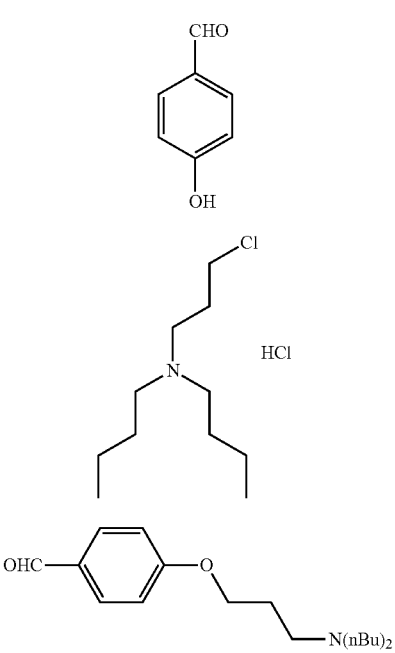

and the obtained compound of formula (V) is isolated and, if desired, converted into a pharmaceutically acceptable salt thereof.

This reaction is typically carried out in a solvent or in a mixture of solvents. The solvent is typically selected from the group of ketones, esters and any mixtures thereof.

Specific examples include, among others, methyl ethyl ketone or ethyl acetate.

The reaction is typically carried out in the presence of a base. Said base is typically selected from the group of alkali carbonates, e.g. potassium carbonate.

The reaction temperature may range from room temperature to the boiling point of the reaction mixture, typically a heating to 70-90° C. is applied.

Compounds of formula (II) and (IV) are known from WO 02/48132 (Sanofi).

Compound of formula (III) is commercially available.

Step (a) of the process of the invention is carried out in the presence of a strong acid or base catalyst. Examples of the catalysts are trifluoracetic acid and butyl lithium.

Typically, step (a) is carried out in a solvent. The solvent may be an inert solvent (e.g. hexane, THF or MeTHF) or may serve as the catalyst (e.g. trifluoracetic acid).

The oxidation of step (b) is typically carried out in a solvent, in the presence of an oxidizing agent. The oxidizing agents can be for example sodium hypochlorite or hydrogen peroxide in aqueous acidic medium. If desired, the excess of the oxidizing agent (e.g. sodium hypochlorite) can be neutralized by using e.g. sodium bisulfite.

In the above reactions the temperature is chosen according to the general practice of a person skilled in organic chemistry. Applicable temperature values can be found in the examples.

The reaction steps are generally carried out under atmospheric pressure.

In the processes for the preparation of the intermediary compounds of formula (V) and (VI) the product is typically isolated as a base. If desired, the isolated base can be converted into a salt (acid addition salt) thereof, which is typically a pharmaceutically acceptable salt (possible acids are mentioned below). Theoretically the acid addition salt can be prepared directly if the relating acid is in the final reaction mixture from which the solid product is made (however, this way is not applied in case of these compounds where the base type form has practical importance).

The applicable acid for the preparation of pharmaceutically acceptable salts can be any inorganic or organic acid which forms an acid addition salt with the compound of general formulae (I), (V) and (VI). Exemplary acids which can form an acid addition salt are as follows: acetic acid, adipic acid, alginic acid, ascorbic acid, aspartic acid, benzoic acid, benzenesulfonic acid, boric acid, butyric acid, citric acid, ethanesulfonic acid, fumaric acid, hydrogen chloride, hydrogen bromide, hydrogen iodide, 2-hydroxyethanesulfonic acid, maleic acid, oxalic acid, methanesulfonic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compounds of general formulae (I) and (VI) (see the "left side" of the molecules) a salt formation can be carried out (on the amide part of it) by a strong base, e.g. an alkaline hydroxide, typically by sodium hydroxide.

However, these salts have less practical importance, but they are within the scope of salts. It means that the phrase "salts" embraces both the acid addition salts and the salts formed by bases (basic salts) in case of compounds of formula (I).

The following non-limiting examples further illustrate the invention.

In the examples the following HPLC method was applied for the determination of the purity of the reaction products:

Column: Waters Symmetry C18 4.6×150 mm, 5 μm
Mobile phases:
Mobile phase A: 5 mM sodium phosphate buffer, pH=2.2
Mobile phase B: acetonitrile
Mobile phase C: methanol
Column temp: 25° C.
Auto sampler temp: 20° C.
Gradient:

| Time (min) | A (%) | B (%) | C (%) |
|---|---|---|---|
| 0 | 65 | 30 | 5 |
| 20 | 40 | 50 | 10 |
| 45 | 15 | 75 | 10 |
| 47 | 65 | 30 | 5 |
| 57 | 65 | 30 | 5 |

Injection vol: 10 μL
Flow rate: 1.5 mL/min
Run time: 57 min
Detection: 245 nm

PREPARATION

Preparation 1

4-(3-dibutylamino-propoxy)-benzaldehyde (V)

9.69 g of dibutylamino propylchloride HCl salt (IV) (0.04 mol, 1 eq), 5 g of 4-hydroxybenzaldehyde (III) (0.04 mol, 1 eq), 17 g of potassium carbonate (0.12 mol, 3 eq) and 30 mL of MEK are added to the reaction flask. The suspension is heated to 80° C. and it is stirred for 10 hours at this temperature. Then the mixture is cooled to room temperature, 40 mL of water is added and the brown solution is stirred for 30 min. After phase separation the organic phase is washed with 15 mL of water and the solvent is evaporated to obtain 10.6 g of compound (V) as a yellowish-brown solid (89%).
Purity by HPLC: 99.4%.
M.p.: 78-80° C.
$^1$H NMR (CDCl$_3$): 9.20 (s, 1H); 7.85 (d, J=8.7 Hz, 2H); 7.12 (d, J=8.8 Hz, 2H); 2.65 (m, 6H); 1.90-0.94 (m, 18H).

EXAMPLES

Example 1

N-(2-butyl-3-{[4-(3-dibutylamino-propoxy)-phenyl]-hydroxymethyl}-benzofuran-5-yl)-methanesulfonamide (VI)

2.67 g of N-(2-butyl-1-benzofuran-5-yl)methanesulfonamide (II) (0.01 mol, 1 eq) is dissolved in 35 mL of n-hexane and 7 mL of 2.5 M BuLi hexane solution is added in 30 min during which the temperature is kept at 20° C. The reaction mixture is stirred for 2 hours at room temperature and then it is added to the solution of 4.37 g of 4-(3-dibutylamino-propoxy)-benzaldehyde (V) (0.015 mol, 1.5 eq) in 80 mL of THF. The reaction mixture is stirred at room temperature for 2 hours and then 40 mL of NH$_4$Cl solution is added. After 15 min of stirring, the product is extracted with 2×40 mL of diethyl ether. The organic phase is concentrated and the crude product is purified by column chromatography (spheric silica; eluent:toluene:MTBE:methanol=50:40:10) to obtain 2.24 g of compound (VI) (40%).
Purity by HPLC: 97.9%.
Molecular weight (calc): 558.7747 Da; (measured): 558.7741 Da.
$^1$H NMR (DMSO): 7.68 (d, J=8.5 Hz, 2H); 7.24 (m, 3H); 6.90 (d, J=8.5 Hz, 2H); 5.45 (s, 1H); 4.88 (s, 1H); 4.10 (t, J=6.1 Hz, 2H); 2.90 (s, 3H); 2.78 (t, J=7.0 Hz, 2H); 2.54 (t, J=7.0 Hz, 2H); 2.47 (s, 1H); 2.36 (t, J=7.0 Hz, 4H); 1.90 (m, 2H); 1.60-1.70 (m, 2H); 1.4-1.45 (m, 10H); 0.8-0.9 (m, 9H).

Example 2

N-(2-butyl-3-{[4-(3-dibutylamino-propoxy)-phenyl]-hydroxymethyl}-benzofuran-5-yl)-methanesulfonamide (VI)

5.34 g of N-(2-butyl-1-benzofuran-5-yl)methanesulfonamide (II) (0.02 mol, 1 eq) is dissolved in 40 mL of trifluoroacetic acid and 8.7 g of 4-(3-dibutylamino-propoxy)-benzaldehyde (V) (0.03 mol, 1.5 eq) is added to the solution. The reaction mixture is heated to 40° C. and stirred for 10 hours at this temperature. The mixture is cooled to room temperature and 100 mL of water is added. After 15 min of stirring, the product is extracted with 2×50 mL of dichloromethane. The organic phase is concentrated and the crude product is purified by column chromatography (spheric silica; eluent:toluene:MTBE:methanol=50:40:10) to obtain 3.68 g of compound (VI) (33%).
Purity by HPLC: 97.3%.
The product is identical with the compound prepared in Example 1.

Example 3

N-[2-butyl-3-[4-[3-(dibutylamino)propoxy]benzoyl]-1-benzofuran-5-yl]-methanesulfonamide (1)

5.59 g of N-(2-butyl-3-{[4-(3-dibutylamino-propoxy)-phenyl]-hydroxymethyl}-benzofuran-5-yl)-methanesulfonamide (VI) (0.01 mol, 1 eq) is dissolved in 30 mL of glacial acetic acid. 10 mL of 2.0 M aqueous sodium hypochlorite solution is added in 30 min. The mixture is stirred for 2 hours at room temperature and then 5 mL of sodium bisulfite solution is added. After 15 min of stirring, the mixture is poured to 100 mL of water and the product is extracted with 2×50 mL of dichloromethane. The solvent is evaporated and the crude product is purified by column chromatography (spheric silica; eluent:toluene:ethyl acetate=70:30) to obtain 1.56 g of dronedarone (I) (28%).
Purity by HPLC: 99.3%.
$^1$H NMR (DMSO): 7.72 (d, J=8.6 Hz, 2H); 7.27 (m, 3H); 6.90 (d, J=8.6 Hz, 2H); 5.52 (s, 1H); 4.07 (t, J=6.2 Hz, 2H); 2.91 (s, 3H); 2.78 (t, J=7.0 Hz, 2H); 2.55 (t, J=7.0 Hz, 2H); 2.39 (t, J=7.0 Hz, 4H); 1.90 (m, 2H); 1.60-1.70 (m, 2H); 1.4-1.45 (m, 10H); 0.8-0.9 (m, 9H).

Example 4

N-[2-butyl-3-[4-[3-(dibutylamino)propoxy]benzoyl]-1-benzofuran-5-yl]-methanesulfonamide (I)

5.59 g of N-(2-butyl-3-{[4-(3-dibutylamino-propoxy)-phenyl]-hydroxymethyl}-benzofuran-5-yl)-methanesulfonamide (VI) (0.01 mol, 1 eq) is dissolved in 40 mL of glacial acetic acid. 15 mL of 30% hydrogen peroxide solution is added in 1 hour at room temperature and the reaction mixture is stirred for 36 hours. 80 mL of water is added to the reaction mixture and the product is extracted with 50 mL of dichloromethane. The organic phase is concentrated and the crude product is purified by column chromatography (spheric silica; eluent:toluene:ethyl acetate=70:30) to obtain 4.34 g of dronedarone (I) (78%).

Purity by HPLC: 99.7%.

The product is identical with the compound prepared in Example 3.

The invention claimed is:

1. A process for the preparation of dronedarone (I)

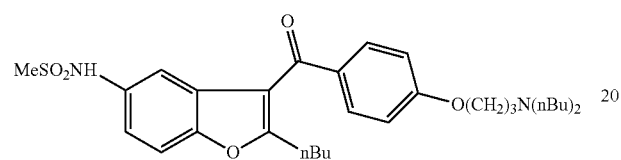
(I)

or a pharmaceutically acceptable salt thereof comprising the steps of:
(a) oxidizing a compound of formula (VI) or a salt thereof,

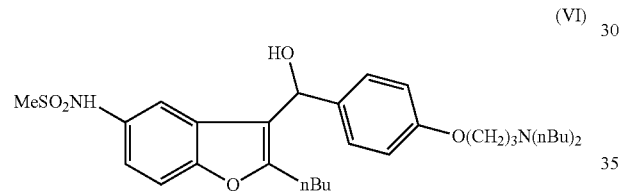
(VI)

(b) isolating the obtained product, and
(c) optionally converting the product into a pharmaceutically acceptable salt thereof.

2. The process according to claim 1, wherein the oxidation is carried out with sodium hypochlorite or hydrogen peroxide in aqueous acidic medium.

3. A process for the preparation of dronedarone (I)

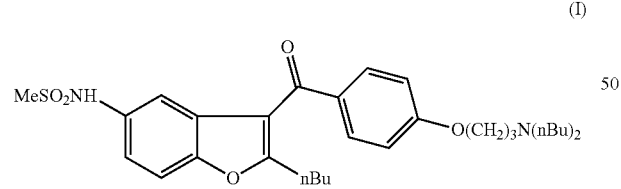
(I)

or a pharmaceutically acceptable salt thereof according to claim 1 comprising
(a) reacting the compound of formula (II)

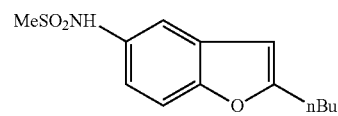
(II)

is reacted with the compound of formula (V)

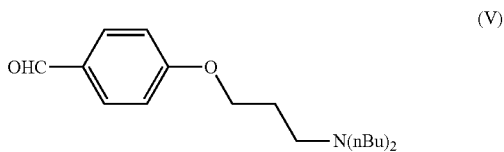
(V)

in the presence of strong acid or base catalyst to obtain the compound of formula (VI)

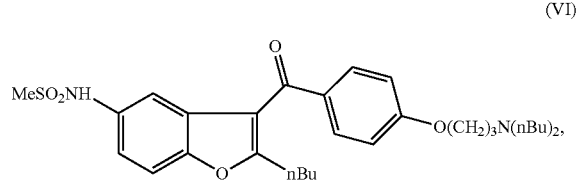
(VI)

(b) oxidizing the compound of formula (VI)

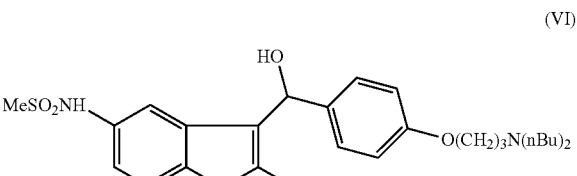
(VI)

to obtain dronedarone (I)

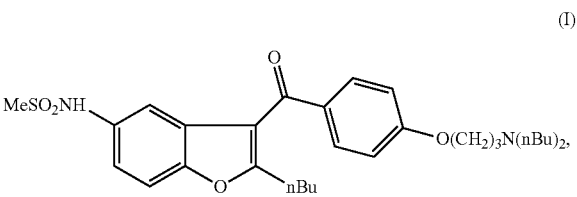
(I)

(c) isolating the obtained product, and
(d) optionally converting the product into a pharmaceutically acceptable salt thereof.

4. A process for the preparation of dronedarone (I)

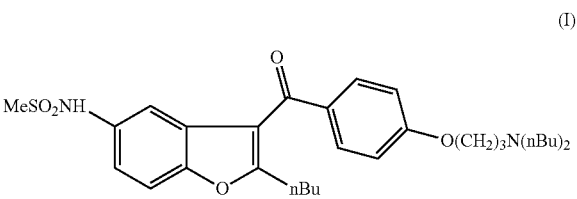
(I)

or a pharmaceutically acceptable salt thereof according to claim 2, comprising (a) reacting the compound of formula (II)

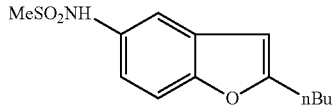

(II)

with the compound of formula (V)

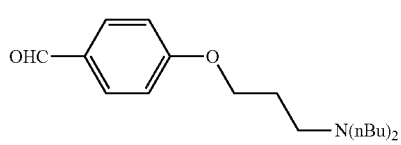

(V)

in the presence of strong acid or base catalyst to obtain the compound of formula (VI)

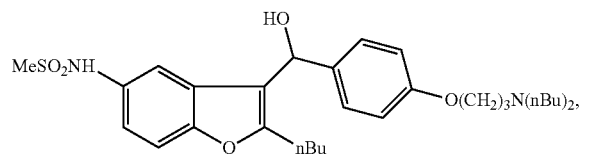

(VI)

(b) oxidizing the compound of formula (VI)

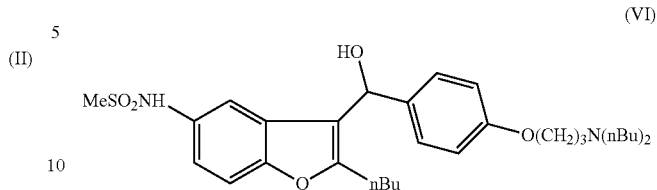

(VI)

to obtain dronedarone (I)

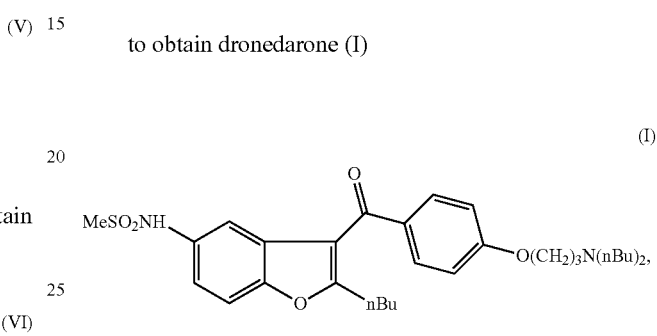

(I)

(c) isolating the obtained product, and (d) optionally converting the product into a pharmaceutically acceptable salt thereof.

* * * * *